United States Patent [19]

Elango

[11] Patent Number: 5,300,675
[45] Date of Patent: Apr. 5, 1994

[54] PROCESS FOR SYNTHESIZING SUBSTITUTED CINNAMIC ACID DERIVATIVES

[75] Inventor: Varadaraj Elango, Norwood, Mass.

[73] Assignee: Hoechst Celanese Corp., Somerville, N.J.

[21] Appl. No.: 85,262

[22] Filed: Jun. 29, 1993

[51] Int. Cl.$^5$ .............................................. C07C 69/76
[52] U.S. Cl. ............................ 560/55; 560/104; 558/414
[58] Field of Search ............... 560/104, 55; 558/414

[56] References Cited

U.S. PATENT DOCUMENTS

| | | | |
|---|---|---|---|
| 3,626,005 | 12/1971 | Scheben et al. | 560/104 |
| 4,311,706 | 1/1982 | Bodor | 424/301 |
| 4,578,507 | 3/1986 | Wada | 560/104 |
| 4,970,332 | 11/1990 | Caskey | 560/104 |

*Primary Examiner*—Paul J. Killos
*Attorney, Agent, or Firm*—Palaiyor S. Kalyanaraman

[57] ABSTRACT

This invention discloses a novel process for preparing cinnamic acid derivatives. The inventive process is illustrated by the synthesis of 2-ethylhexyl p-methoxycinnamate by coupling p-methoxybenzenediazonium tetrafluoroborate with 2-ethylhexyl acrylate in an alcohol solution, wherein a buffer compound such as sodium acetate is present, the coupling reaction being catalyzed by a mixture comprising a copper salt, such as cuprous chloride, and a palladium salt, such as $Li_2PdCl_4$.

18 Claims, No Drawings

PROCESS FOR SYNTHESIZING SUBSTITUTED CINNAMIC ACID DERIVATIVES

FIELD OF THE INVENTION

This invention relates to a novel synthetic process to prepare substituted cinnamic acid derivatives.

BACKGROUND OF THE INVENTION

Cinnamic acid derivatives are important commercial materials, with diverse uses such as, for example, antioxidants in plastics, ultraviolet absorbers, pharmaceutical intermediates and the like. Several cinnamate esters find applications as ingredients in sunscreen formulations. See, for example, *Kirk-Othmer Encyclopedia of Chemical Technology*, Wiley-Interscience, New York, Vol. 7, page 153 (1979). An example cinnamate ester that has high commercial value is 2-ethylhexyl p-methoxycinnamate (EHMC) (Formula 1).

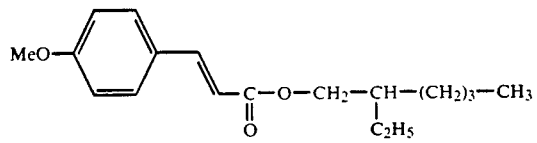

Processes to synthesize cinnamic acid derivatives are known. For example, a process to make EHMC involves coupling of an arenediazonium salt with an unsaturated compound under palladium catalysis. A review of this approach is provided by R. F. Heck, *Palladium Reagents in Organic Synthesis*, Academic Press, London, 287-290 (1985).

U.S. Pat. No. 4,970,332 discloses a process to make EHMC wherein p-anisidine is first diazotized and converted to p-iodoanisole. p-Iodoanisole is then reacted with 2-ethylhexyl acrylate in the presence of a trialkylamine and a palladium catalyst. EHMC and trialkylaminehydroiodide are produced in the reaction which are then separated.

Other pertinent publications in this area include K. Kikukawa et al, *J. Organometallic Chem.*, Vol. 270, pages 277-282 (1984), which describes coupling of arenediazonium tetrafluoroborates with vinylsilanes using palladium catalysts. XU Jian-Hua et al, *Organic Chemistry (Youji Huazue)*, No. 6, pages 452-454 (1987) describe $Li_2PdCl_4$—CuCl catalyzed coupling of arenediazonium tetrafluoroborates with methyl acrylate in methanol to yield cinnamic acid derivatives.

A problem with such coupling reactions of arenediazonium compounds with alkenes is the poor yield of the desired cinnamic acid derivatives. Generally in these reactions, an acid such as, for example, tetrafluoroboric acid is formed as a byproduct. This acid then polymerizes the alkene reactant to polymeric products. This side action reduces the availability of the alkene for the desired coupling reaction.

Due to the commercial significance of cinnamic acid derivatives, there is a continuing interest in overcoming the above-mentioned problem as well as in discovering new synthetic processes to prepare them economically and from readily available ingredients, in high yields and purity.

SUMMARY OF THE INVENTION

It has been found that palladium/copper catalyzed coupling reactions of arenediazonium compounds with suitable acrylic acid derivatives, when conducted in a solution of a suitable buffer compound in a suitable solvent, can result in substantially higher yields of cinnamic acid derivatives. When combined with the well known formation of diazonium compounds from aromatic amines, this sequence gives a very convenient method of preparing cinnamic acid derivatives in high yields. Furthermore, the inventive process advantageously affords recovery and recycling of catalysts and aqueous effluents.

The reactions according to the present invention may be illustrated by a process to prepare cinnamate esters of Formula 4 from aromatic amines of Formula 2 as shown in Scheme 1.

Scheme 1

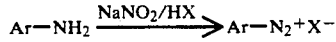

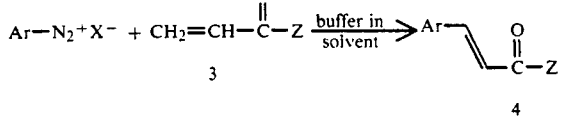

In Scheme 1, Ar is a phenyl ring substituted in one or more positions, wherein the said substituents are branched or unbranched $C_1$-$C_6$ alkyl, $C_1$-$C_6$ alkoxy, carboxy, halogen or cyano; and Z is $OR_1$ or $NR_2R_3$, wherein $R_1$ is branched or unbranched $C_1$-$C_{18}$ alkyl, unsubstituted or substituted aryl or arylalkyl, and $R_2$ and $R_3$ are independently H or unbranched or branched $C_1$-$C_{18}$ alkyl, unsubstituted or substituted aryl or arylalkyl. HX represents an inorganic or organic acid. When Ar is 4-methoxyphenyl and Z is 2-ethylhexyloxy, the product will be EHMC.

The process thus comprises first preparing the diazonium salt of the amine 2, using an inorganic nitrite such as, for example, sodium nitrite, or an organic nitrite such as, for example, t-butyl nitrite, in the presence of an aqueous acid, e.g., tetrafluoroboric acid, at from about −70° C. to about 75° C., and then coupling that diazonium salt with a suitable acrylic acid derivative of Formula 3 in the presence of a mixture of a copper salt, a palladium compound, and a suitable buffer compound in a suitable solvent, between about −70° C. to about 75° C., to yield the desired cinnamic acid derivative.

DESCRIPTION OF THE PREFERRED EMBODIMENTS

In one embodiment, this invention discloses an improve process for the preparation of substituted cinnamic acid derivatives as outlined above. In another embodiment, the invention discloses an improved process for preparing EHMC from p-anisidine (Formula 2, Ar=p-methoxyphenyl). Both embodiments generally consist of two steps, which may advantageously be combined, if so desired. For synthesizing cinnamic acid derivatives, in the first step, the aromatic amine is diazotized to prepare a diazonium salt of the amine. Diazotization reactions are well known in the art. The instant diazotization reaction is conducted in aqueous solution at temperatures of about 70° to about 55° C., using an inorganic or organic nitrite and a suitable acid. Examples of inorganic nitrites useful in the invention include sodium nitrite, potassium nitrite, cesium nitrite, and the like. Examples of useful organic nitrites include t-butyl nitrite, amyl nitrite, and the like. Examples of suitable acids include inorganic acids such as, for example, hydrochloric acid, sulfuric acid, tetrafluoroboric acid, and the like, and organic acids such as, for example, acetic acid, methanesulfonic acid, and the like. The instant reaction is preferably performed using sodium nitrite in aqueous tetrafluoroboric acid, when the diazonium tetrafluoroborate is formed. Alternately, the diazotization reaction may be performed using sodium nitrite and aqueous sulfuric acid to form the diazonium hydrosulfate, which may then be reacted with sodium tetrafluoroborate to yield the diazonium tetrafluoroborate. If p-anisidine is the starting amine, the diazonium salt is p-methoxybenzenediazonium tetrafluoroborate.

For the diazotization reaction, generally the amine and the nitrite are employed in a mole ratio from about 1:1 to about 1:2 respectively, typically from about 1:1 to about 1:1.5, and preferably from about 1:1 to about 1:1.1. The acid is resent in the range of generally about 1-4 moles, typically about 1-3 moles and preferably about 1 mole of acid to 1 mole of the nitrite. However, when the proton equivalent of the acid is higher, then the acid amount is adjusted accordingly. Thus, for example, if a diprotic acid such as sulfuric acid is used, then the preferred amount above becomes about 0.5 mole of the acid to 1 mole of the nitrite. The diazotization reaction is carried out at a temperature of from about −70° C. to about 75° C. generally, from about −40° C. to about 60° C. typically, and from about −20° C. to about 50° C. preferably, for a time period ranging from about 0.1 to about 24 hours.

The diazonium salt is then coupled with an acrylic acid derivative (Formula 3) to form the desired cinnamic acid derivative. The diazonium salt and the acrylic acid derivative are generally employed in a mole ratio from about 1:0.8 to about 1:3, typically from about 1:1 to about 1:2, and preferably from about 1:1 to about 1:1.3. If EHMC is the desired product, 2-ethylhexyl acrylate is used as the acrylic acid derivative. The reaction is performed in a suitable solvent, wherein a suitable buffer compound is present, under catalysis by a mixture containing a copper salt and a palladium compound. Suitable solvents are described below. The use of the buffer compound in the coupling reaction surprisingly offers a substantially higher yield of the desired cinnamate. The reaction is conducted at temperatures generally in the range of about 70° C. to about 75° C., typically about −30° C. to about 60° C., and preferably about −20° C. to about 50° C., for a time period ranging from 0.1 to 24 hours, preferably 0.2 to about 6 hours.

The coupling reaction employs a catalyst mixture containing a copper salt and a palladium compound. Suitable copper salts include cuprous chloride, cuprous acetate, and the like. Suitable palladium compounds include $Pd[P(Phenyl)_3]_4$, $Li_2PdCl_4$, $Na_2PdCl_4$, and the like. $Li_2PdCl_4$ may be prepared by mixing one mole of $PdCl_2$ with 2 moles of LiCl in an alcohol solvent such as methanol, as described by A. Kasahara et al, *Bull. Chem. Soc. Japan*, page 1220 (1973). The copper salt is generally used in the amounts of about 0.0001-0.1 mole and the palladium compound in the amounts of about 0.0001-0.01 mole per mole of the diazonium salt.

A significant feature of the inventive process is the use of the buffer compound. Suitable buffer compounds are carboxylate salts of alkali metals such as, for example, sodium acetate, potassium acetate, sodum amylate, sodium citrate and the like. Preferred are the acetates, e.g., sodium acetate, potassium acetate and cesium acetate. A solution of the buffer compound such as, for example, sodium acetate, in a suitable solvent may be separately prepared and added to the reaction medium in appropriate quantities, or it may be advantageously prepared in situ when the buffer compound is added in suitable amounts to the reaction ingredients contained in the suitable solvent. Suitable amounts of the buffer compound in the reaction medium are generally in the range of about 0.1-2.5 moles, typically about 0.2-2 moles, and preferably about 0.5-1.5 moles per mole of diazonium compound.

Suitable solvents for the reaction are protic organic solvents such as, for example, alcohols, carboxylic acids, or mixtures thereof. Alcohols are preferred. Suitable alcohol solvents include methanol, ethanol, isopropanol, and the like. The solvent is present generally in the range of from about 0.1 to about 3 liters, preferably from about 0.25 to about 1.5 liters, and typically form about 0.5 to about 1.0 liters, per mole of the diazonium compound. In absence of a protic solvent, yields of cinnamic acid derivatives are generally low. Thus, for example, in the coupling of p-methoxybenzenediazonium tetrafluoroborate with 2-ethylhexyl acrylate employing a buffer according to the invention, if a solvent such as acetonitrile or acetone is employed instead of an alcohol, generally no reaction occurs, or even when there is reaction, low yields of EHMC are obtained.

A typical inventive reaction sequence may he illustrated by the following process to prepare EHMC from p-anisidine. First, the diazonium salt of p-anisidine is prepared by known methods. Thus, p-Anisidine may be dissolved in an aqueous acid such as, for example, 48% $HBF_4$, and cooled to about 0°-10° C. A cooled (0°-10° C.) solution of, for example, sodium nitrite in water is added to it slowly and stirred for about 30-60 minutes to complete the formation of p-methoxybenzenediazonium tetrafluoroborate. This compound may be precipitated by adding methanol, filtered and dried. Care should be taken not to heat the diazonium compound to temperatures above, for example, 40° C., since diazonium compounds are generally unstable at such temperatures.

The inventive coupling reaction may be illustrated as follows. The above diazonium compound may be added to a solution of sodium acetate in a solvent such as, for example, methanol. Then, 2-Ethylhexyl acrylate, a solution of $Li_2PdCl_4$ (prepared from LiCl and $PdCl_2$ in methanol), and cuprous chloride are added in that order. Stirring at room temperature for about 1-5 hours generally completes the reaction. The product EHMC may be isolated by filtering off the inorganic salts, and removing the solvents in vacuo. Yields in excess of 70% are usually obtained.

Another embodiment of the resent invention is the recovery and recycle of the catalysts and the aqueous process effluents. In a typical coupling reaction illustrated above, the reaction mixture generally contains the cinnamic acid derivative, solvent or solvents, salts derived from buffer and catalyst metal. The solvent is reclaimed from the reaction mixture by conventional methods such as, for example, distillation. Then the desired cinnamic acid derivative is separated by suitable processes such as, for example, filtration, extraction and the like. If the product is a liquid, for example, it is preferably separated from the solid wastes by filtration, and then isolated and purified from the filtrates by distillation.

The solid wastes containing salts derived from spent catalysts and buffer are processed for recovery and recycle. This process involves the separation of salts such as, for example, $PdCl_2$, $CuCl_2$, and the like, from other salts such as, for example, NaCl, $NaBF_4$, and the like. The precious metals are precipitated from an aqueous solution by using suitable complexing agents, well known to those skilled in the art. Preferred complexing agents are sodium dimethyl dithiocarbamate, sodium diethyl dithiocarbamate, and the like. The complexing agents are generally used in the range of about 0.2-3 moles, preferably about 0.25-5 moles, and typically about 0.5-1.0 moles per mole of copper and palladium salts used in the coupling reaction. The precipitation of the copper and palladium salts is generally carried out at around ambient temperature for a period ranging from about 0.1 to about 2 hours. The precipitate is generally separated from the aqueous effluent by processes such as, for example, filtration, and may then be processed for metal recovery by techniques well known to those skilled in the art.

The aqueous effluent containing primarily sodium salts such as sodium tetrafluoroborate derived from the diazonium tetrafluoroborate may then be recycled to the diazotization process, thus minimizing the effluent discharge.

When the above coupling reaction is performed without the sodium acetate buffer, the yields of EHMC are substantially reduced. In a typical set of experiments, a coupling reaction was run according to the present invention using p-methoxybenzenediazonium tetrafluoroborate and 2-ethylhexylacrylate in methanol using cuprous chloride and $Li_2PdCl_4$, and a buffer compound such as sodium acetate as described above. Yields of EHMC in excess of 70% were obtained. A comparative example was done following the procedure described by XU Jian-Hua et al, referred to above. This process did not use any buffer in the coupling reaction. Yields of EHMC were only about 40%, thus demonstrating the superiority of the resent process using buffered reaction conditions.

The following Examples are provided in order to further illustrate the present invention; however, the invention is in no way limited thereby.

EXAMPLES

In the following Examples, g refers to grams, ml to milliliters, ° C. to degrees Celsius, m to moles, mmoles to millimoles, and ambient temperature to temperatures about 21°-29° C.

Example 1: Preparation of p-methoxybenzenediazonium tetrafluoroborate p-Anisidine (30.75 g, 0.25 mole) was dissolved in aqueous tetrafluoroboric acid (48%, 110 ml) in a 500 ml 3 necked flask fitted with mechanical stirring, and cooled to 0°-10° C. Sodium nitrite (17.5 g, 0.25 mole) was separately dissolved in water (34 ml) and the solution cooled to 5°-10° C., and was then added dropwise to the reaction mixture over 60 minutes. The reaction mixture was stirred for about 45 minutes at 0°-10° C., and then tested with starch-iodide paper for excess nitrous acid. Any excess nitrous acid was destroyed by adding a small amount (approx. 0.1 g.) of sulfamic acid. The precipitate was filtered, washed once with ice-cold water (about 30 ml), and then twice with methanol (20 ml each time). The product diazonium tetrafluoroborate was dried under vacuum at ambient temperature. Yield 45.4 g (about 82%). This could be purified by dissolving in minimum amount of acetone, and precipitating with ether, repeating this process three times. The final product was filtered, washed with ether (30 ml), and dried.

Example 2: Preparation of 2-ethylhexyl p-methoxycinnamate under buffered reaction conditions: (a) Preparation of $Li_2PdCl_4$ $PdCl_2$ (1.77 g, 10 mmole) was added to a solution of LiCl (0.84 g, 20 mmole) in methanol (100 ml) at ambient temperature and stirred under nitrogen for about 48 hours, then transferred to and stored in a septum bottle under nitrogen for use as needed.

(b) Coupling of p-methoxybenzenediazonium tetrafluoroborate with 2-ethylhexyl acrylate: The diazonium compound from Example 1 (2.2 g, 10 mmole) was added to a solution of sodium acetate (0.998 g, 12.2 mmole) in methanol (10 g) to yield a suspension. 2-Ethylhexyl acrylate (2.09 g, 11 mmole) was added to the reaction mixture, followed by the $Li_2PdCl_4$ solution above (1 ml, 0.1 mmole), and cuprous chloride (0.052 g. 0.52 mmole) in that order. Nitrogen evolution was observed immediately. The reaction mixture was stirred at ambient temperature until nitrogen evolution ceased (about 2 hours). The reaction pH was found to be 5.4 at the end of this time. The reaction mixture was then concentrated to remove methanol. Ethyl acetate (100 ml) was added, and it was filtered to remove sodium tetrafluoroborate and other insolubles. The organic filtrate was transferred to a separatory funnel, washed successively with aqueous potassium carbonate solution (20%, 50 ml), and water (50 ml), then dried with anhydrous $MgSO_4$, filtered, and concentrated to yield the product (EHMC) Yield: 82%.

Example 3: Comparative Example, Formation of EHMC under non-buffered reaction conditions The coupling reaction outlined in Example 2 was performed without the sodium acetate. Thus, the diazonium compound from Example 1 was reacted in methanol with 2-ethylhexyl acrylate, to which cuprous chloride and $Li_2PdCl_4$ catalyst solution were added. Nitrogen evolution was observed as before. After the nitrogen evolution ceased, the reaction mixture was worked up as in Example 2 to obtain EHMC in a yield of 41.6%.

Example 4: Preparation of EHMC and Recovery and Recycle of Catalysts and aqueous effluents Concentrated sulfuric acid (235.0 g, 2.4 m) and water (55 ml) were taken in a 2 liter 3-necked flask fitted with a mechanical stirrer, to which p-anisidine (147.0 g, 1.19 m) was added and dissolved and the solution was cooled to 0°-10° C. $NaNO_2$ (91.0 g, 1.3 m) was separately dissolved in water (155 ml) and the solution was cooled to 5°-10° C., and then added dropwise to the reaction over about 60 minutes. The reaction mixture was then stirred for about 45 minutes, and then tested for nitrous acid with a starch-iodide paper. Any excess nitrous acid was destroyed by adding about 0.3 g of sulfamic acid. $NaBF_4$ (197.5 g, 1.8 m) was dissolved in water (200 ml) and added to the reaction mixture. The resulting slurry was stirred for about 10 minutes at 0°-5° C. and filtered. The precipitate was washed once with ice cold water (100 ml) and then once with cold methanol (100 ml). The product, p-methoxybenzenediazonium tetrafluoroborate, was dried in vacuum at ambient temperature. Yield: 239.0 g (90%).

Methanol (700 g) was taken in a 2 liter 3 necked flask fitted with a mechanical stirrer, condenser, thermometer and gas outlet. Sodium acetate (106.2 g, 1.3 m) was added to the flask and dissolved. The above diazonium tetrafluoroborate was added to yield a suspension. 2-Ethylhexyl acrylate (237.0 g, 1.3 m) was added to the reaction mixture. $Li_2PdCl_4$ (1.0 g, 5.4 mmol) in methanol (50 ml) was then added, followed by cuprous chloride (2.15 g, 22 mmol). Nitrogen evolution was observed immediately. The reaction mixture was stirred at ambient temperature until nitrogen evaluation ceased (about 4 hours). The reaction pH was found to be 5.4 at the end. The reaction mixture was then concentrated to remove methanol. Ethyl acetate (200 ml) was added and the reaction mixture filtered to remove inorganic salts. EHMC was isolated from the filtrate by distilling off the solvent. Yield: 250.0 g (80%).

The inorganic salts filtered above were dissolved in water (500 ml) and sodium dimethyl dithiocarbamate (6.5 g, 55 mmol) was added to precipitate palladium and copper. The precipitate (6.6 g, 100% metal recovery) was collected by filtration, dried and processed by known processes. The aqueous effluent contained primarily sodium tetrafluoroborate which could be used in subsequent diazotization reactions.

What is claimed is:

1. A process for preparing a substituted cinnamic acid derivative of the formula Ar—CH=CH—CO—Z, the process comprising: reacting a diazonium salt of an aromatic amine of the formula Ar—$NH_2$ with an acrylic acid derivative of the formula $CH_2$=CH—CO—Z in a suitable organic solvent containing a suitable buffer compound, the reaction being catalyzed by mixture comprising a copper salt and a palladium compound, at a reaction temperature of from about −70° C. to about 75° C., wherein Ar is a phenyl ring substituted in one or more positions, wherein the substituents are branched or unbranched $C_1$-$C_6$ alkyl, $C_1$-$C_6$ alkoxy, carboxy, halogen or cyano; Z is $OR_1$ or $NR_2R_3$, wherein $R_1$ is branched or unbranched $C_1$-$C_{18}$ alkyl, unsubstituted or substituted aryl or arylalkyl, and $R_2$ and $R_3$ are independently selected from the group consisting of H, unbranched or branched $C_1$-$C_{18}$ alkyl and unsubstituted or substituted aryl or arylalkyl.

2. The process as described in claim 1, wherein Ar is p-methoxyphenyl, and Z is 2-ethylhexyloxy.

3. The process as described in claim 1, wherein Ar is o-methoxyphenyl, and Z is 2-ethylhexyloxy.

4. The process as described in claim 1, wherein said buffer compound is the carboxylate of an alkali metal.

5. The process as described in claim 4, wherein said alkali metal carboxylate is selected from the group consisting of sodium acetate, potassium acetate, cesium acetate, sodium amylate and sodium citrate.

6. The process as described in claim 5, wherein said buffer compound is sodium acetate.

7. The process as described in claim 1, wherein said buffer compound is present in an amount of about 0.1-2.5 moles per mole of said diazonium salt.

8. The process as described in claim 1, wherein said solvent is a protic organic solvent.

9. The process as described in claim 8, wherein said protic organic solvent is an alcohol.

10. The process as described in claim 9, wherein said alcohol is selected from the group consisting of methanol, ethanol, and isopropanol.

11. The process as described in claim 10, wherein said alcohol is methanol.

12. The process as described in claim 1, wherein said copper salt is cuprous chloride.

13. The process as described in claim 1, wherein said palladium compound is selected from the group consisting of $Pd[P(Ph)_3]_4$, $Li_2PdCl_4$, $Na_2PdCl_4$ and $K_2PdCl_4$.

14. The process as described in claim 13, wherein said palladium compound is $Li_2PdCl_4$.

15. The process as described in claim 1, wherein said reaction temperature is from about −20° to about 50° C.

16. The process as described in claim 1, wherein said catalyst mixture is recovered at the end of said coupling reaction.

17. A process for preparing 2-ethylhexyl p-methoxycinnamate, which comprises coupling p-methoxybenzenediazoniumtetrafluoroborate with 2-ethylhexyl acrylate in an alcohol solvent containing a buffer compound, said coupling being catalyzed by a mixture comprising a copper salt and a palladium compound, at a reaction temperature of from about −70° C. to about 75°.

18. The process as described in claim 17, wherein said copper salt is cuprous chloride, said palladium compound is $Li_2PdCl_4$, said buffer compound is sodium acetate, and said alcohol solvent is methanol.

* * * * *